(12) United States Patent
Yamamoto et al.

(10) Patent No.: US 7,735,354 B2
(45) Date of Patent: Jun. 15, 2010

(54) LIQUID-CONDITION DETECTION SENSOR

(75) Inventors: Takashi Yamamoto, Niwa-gun (JP);
Takeo Sasanuma, Komaki (JP);
Yoshikuni Sato, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 510 days.

(21) Appl. No.: 11/653,252

(22) Filed: Jan. 16, 2007

(65) Prior Publication Data
US 2007/0169544 A1    Jul. 26, 2007

(30) Foreign Application Priority Data
Jan. 25, 2006    (JP)    ............... 2006-015737

(51) Int. Cl.
*G01N 33/00*    (2006.01)
(52) U.S. Cl. ..................... 73/61.41; 73/64.56
(58) Field of Classification Search ............... 73/53.01, 73/61.41, 64.56, 304 C
See application file for complete search history.

(56) References Cited

U.S. PATENT DOCUMENTS

| | | | | |
|---|---|---|---|---|
| 5,929,754 | A * | 7/1999 | Park et al. .................. | 340/439 |
| 6,237,412 | B1 | 5/2001 | Morimoto | |
| 6,269,694 | B2 | 8/2001 | Morimoto | |
| 7,064,560 | B2 * | 6/2006 | Yamamoto et al. .......... | 324/663 |
| 7,114,391 | B2 | 10/2006 | Sasaki et al. | |
| 7,337,662 | B2 | 3/2008 | Sato et al. | |
| 2007/0054409 | A1 | 3/2007 | Inoue et al. | |

FOREIGN PATENT DOCUMENTS

| | | |
|---|---|---|
| DE | 19756159 C1 | 6/1999 |
| EP | 1553389 A1 | 7/2005 |
| EP | 1610119 A1 | 12/2005 |
| EP | 1 669 743 A1 | 6/2006 |
| JP | 2005-84026 | 3/2005 |
| JP | 2005084026 A | 3/2005 |
| WO | 9839623 A1 | 9/1998 |

* cited by examiner

*Primary Examiner*—Daniel S Larkin
(74) *Attorney, Agent, or Firm*—Sughrue Mion, PLLC

(57) ABSTRACT

A liquid-condition detection sensor (1) including a sensor element (51), at least a portion of which contacts a urea aqueous solution; connection terminals (52) fixedly attached to the sensor element (51); connection cables (53) which electrically communicate with the concentration sensor element (51) via the connection terminals (52); an inner tube (42) which holds the concentration sensor element (51) at a distal end portion (421) by use of a holder member (55) and surrounds a portion of the connection cables (53) and the entire connection terminals (52); and a separator formed from a material having rubberlike elasticity (54) including a terminal-inner-tube-insulating portion (542) which intervenes between the connection terminals (52) and the inner tube (42) to thereby insulate the connection terminals (52) and the inner rube (42) from one another.

12 Claims, 8 Drawing Sheets

LIQUID-CONDITION DETECTION SENSOR

FIELD OF THE INVENTION

The present invention relates to a liquid-condition detection sensor for detecting the condition of a liquid to be measured.

BACKGROUND OF THE INVENTION

Exhaust gas emitted from automobiles equipped with a diesel engine or the like contains substances such as nitrogen oxides (NOx). In recent years, various measures haven been taken to purify such exhaust gas in order to protect as well as to prevent contamination of the environment. One measure used to purify exhaust gas is an exhaust gas purification apparatus.

Such exhaust gas purification apparatus is mounted in an automobile and decomposes nitrogen oxides (NOx) to render them harmless by means of an NOx selective catalytic reduction (SCR) system. The NOx selective catalytic reduction (SCR) system employs a urea aqueous solution as a reducing agent. The urea aqueous solution is contained in a tank mounted in the automobile. In order to effectively decompose nitrogen oxides (NOx), the concentration of the urea aqueous solution (the concentration of urea in the urea aqueous solution) must be maintained within a specified range.

Even when a urea aqueous solution of appropriate concentration is charged in the tank, the concentration of the urea aqueous solution may fall outside the specified range, due to changes occurring with the passage of time or the like. Also, a worker may erroneously mix light oil or water in the tank. In order to cope with these problems, a device for determining the concentration of urea in the urea aqueous solution contained in the tank has been proposed as a sensor for detecting whether or not the urea aqueous solution is within a suitable concentration range (Patent Document 1).

The urea-concentration-determining device disclosed in Patent Document 1 includes a concentration-determining sensor section and a support section. The concentration-determining sensor section has a concentration-detecting portion, which includes a heating element and a temperature-sensing element, and a liquid-temperature-detecting portion for measuring the temperature of the urea aqueous solution.

The support section is located above the concentration-determining sensor section and has an attachment portion attaching to an opening section of the urea-aqueous-solution tank, a circuit board located above the attachment portion, and a tubular member located below the attachment portion and adapted to hold the concentration-determining sensor section. The circuit board of the support section has a concentration detection circuit and is covered with a cover member. The concentration-detecting portion and liquid-temperature-detecting portion of the concentration-determining sensor section are electrically connected to the circuit board through respective lead wires which extend through the tubular member.

[Patent Document 1] Japanese Patent Application Laid-Open (kokai) No. 2005-84026

In the case where a terminal member is fixedly attached to a sensor element, and an electrical communication member, such as a lead wire or a cable, is connected to the terminal member by soldering or the like, a need may arise for a configuration where at least a portion of the terminal member and at least a portion of the sensor element are disposed within a holder tube (tubular member), and where the holder tube directly or indirectly holds the sensor element so as to prevent entry of liquid into the holder tube.

However, an assembled state of the above configuration may involve a risk of contact and a resultant short circuit between the holder tube and the terminal member. Also, there may be a risk of contact and a resultant short circuit between the holder tube and the sensor element or a risk of cracking or the like in the sensor element. In the case where a plurality of terminal members are present, there may be a risk of contact and a resultant short circuit between the terminal members. Furthermore, vibration or impact during actual use vibrates the sensor element, the terminal member, the lead wire, and the like and consequently generates stress in a connection between the lead wire and the terminal member or a connection between the terminal member and the sensor element. Such vibration or impact potentially induces cracking or a like problem in these connections or portions of the terminal member and the sensor element in the vicinity of the connections.

SUMMARY OF THE INVENTION

The present invention has been made in view of the above-noted problems, and an object thereof is to provide a liquid-condition detection sensor having a terminal member fixedly attached to a sensor element, and a holder tube, which directly or indirectly holds the sensor element at a distal end portion thereof and surrounds at least a portion of the terminal member, and which sensor is adapted to detect the condition of a liquid, the liquid-condition detection sensor being designed to avoid problems due to vibration in an assembled state or during actual use.

The above object of the invention has been achieved by providing a liquid-condition detection sensor, at least a portion of which is to be immersed in a liquid to be measured, and which is adapted to detect a condition of the liquid to be measured. The liquid-condition detection sensor comprises a sensor element, at least a portion of which is to be immersed in the liquid to be measured; a terminal member fixedly attached to the sensor element; an electrically conductive path member connected to the terminal member and electrically communicating with the sensor element via the terminal member; a holder tube extending in a longitudinal direction of the sensor, directly or indirectly holding the sensor element at a distal end portion thereof, and surrounding at least a portion of the electrically conductive path member and at least a portion of the terminal member; and a separator intervening between the terminal member and the holder tube and insulating the terminal member and the holder tube from one another.

The liquid-condition detection sensor of the present invention has a separator which intervenes between the terminal member and the holder tube to thereby insulate the same from one another.

Accordingly, even though this liquid-condition detection sensor is configured such that at least a portion of the terminal member is surrounded by the holder tube, the terminal member and the holder tube are separated from one another, thereby reliably preventing contact and a resultant short circuit therebetween.

Examples of liquid-condition detection sensors include a liquid temperature sensor, a liquid concentration sensor, a sensor for determining the type of liquid present, a sensor for detecting the presence/absence of liquid, a composite sensor of these sensors, and a composite sensor of any of these sensors and another liquid sensor.

No particular limitation is imposed on the electrically conductive path member so long as the member can electrically communicate with the sensor element through mechanical or electrical connection to the terminal member. Examples of the electrically conductive path member include a covered wire in which a core wire such as a strand is covered with a resin such as polyethylene, a lead wire such as an enameled wire, a multicore cable in which a plurality of covered wires (lead wires) are formed into a single cable, and a coaxial cable in which braided wires are arranged coaxially with a core.

The electrically conductive path member and the terminal member can be connected together by soldering or brazing. Alternatively, a portion of the terminal member can be crimped to a lead wire (core). No particular limitation is imposed on the separator so long as the separator can insulate the holder tube and the terminal member from one another. Preferably, the entire separator is made of an insulating material. In view of arrangement of the separator within the holder tube, the separator is preferably made of an insulating material having rubberlike elasticity.

Preferably, the above-mentioned liquid-condition detection sensor is provided with a plurality of the terminal members, and the separator includes an inter-terminal insulating portion intervening between the terminal members and insulating the terminal members from one another.

In the liquid-condition detection sensor of the present invention, the inter-terminal insulating portion of the separator intervenes between the terminal members, thereby insulating them from one another.

Accordingly, the terminal members can be separated from one another, thereby reliably preventing contact and a resultant short circuit therebetween.

Preferably, in either of the above-mentioned liquid-condition detection sensors, the separator is formed from a material having rubberlike elasticity and includes a terminal-holding portion which elastically holds the terminal member within the holder tube.

Even when the liquid-condition detection sensor is subjected to vibration or impact as in the case of being mounted in an automobile, since the terminal-holding portion of the separator elastically holds the terminal member, vibration of the terminal member is suppressed. Accordingly, cracking or a like problem can be appropriately prevented in a connection made by soldering or the like between the terminal member and the electrically conductive path member, in a connection between the terminal member and the sensor element, and in portions of the terminal member and the sensor element in the vicinity of the connections, which cracking or like problem could otherwise result from vibration of the terminal member.

No particular limitation is imposed on the terminal-holding portion of the separator so long as the terminal-holding portion elastically holds the terminal member in a state such that the separator is disposed within the holder tube. Accordingly, the separator may be configured such that the terminal-holding portion elastically holds the terminal member from a time before the separator is disposed within the holder tube.

Alternatively, the separator may be configured as follows. In a state which the separator is not disposed within the holder tube, the terminal-holding portion does not elastically hold the terminal member. However, in a state in which the separator is disposed within the holder tube, the separator is deformed, thereby causing the terminal-holding portion to elastically hold the terminal member. This configuration is particularly preferred since the terminal member and the like can be readily moved within the separator for positioning before the separator is disposed within the holder tube.

Preferably, in any one of the above-mentioned liquid-condition detection sensors, the sensor element is partially surrounded by the holder tube, and the separator includes an element-holding portion which holds the sensor element within the holder tube.

Even when mounted in an automobile so as to subject the liquid-condition detection sensor to vibration or impact, since the element-holding portion of the separator holds the sensor element, vibration of the sensor element is suppressed. Accordingly, the occurrence of cracking or a like problem can be prevented in a connection between the sensor element and the terminal member, in a connection made by soldering or the like between the terminal member and the electrically conductive path member, and in portions of the terminal member and the sensor element in the vicinity of the connections, which could otherwise result from vibration of the sensor element.

In the liquid-condition detection sensor of the invention, the separator including the element-holding portion particularly preferably is formed from a material having rubberlike elasticity such that the element-holding portion elastically holds the sensor element.

Since the separator is formed from a material having rubberlike elasticity to thereby elastically hold the sensor element at the element-holding portion thereof, even when the liquid-condition detection sensor is subjected to vibration or impact, the element-holding portion can absorb the vibration or impact, whereby vibration of the sensor element can be more effectively suppressed. Accordingly, the occurrence of cracking or a like problem can be more effectively prevented in a connection between the sensor element and the terminal member, in a connection made by soldering or the like between the terminal member and the electrically conductive path member, and in portions of the terminal member and the sensor element in the vicinity of the connections.

No particular limitation is imposed on the element-holding portion of the separator so long as the element-holding portion elastically holds the sensor element in a state in which the separator is disposed within the holder tube. Accordingly, the separator may be configured such that the element-holding portion elastically holds the sensor element from a time before the separator is disposed within the holder tube. Alternatively, the separator may be configured as follows. When the separator is not disposed within the holder tube, the element-holding portion does not elastically hold the sensor element. However, when the separator is disposed within the holder tube, the separator is deformed, thereby causing the element-holding portion to elastically hold the sensor element. This configuration is particularly preferred since, before the separator is disposed within the holder tube, the sensor element and the like can be readily positioned within the separator.

Preferably, in the above-mentioned liquid-condition detection sensor, the sensor element is partially surrounded by the holder tube; the separator is formed from a material having rubberlike elasticity having a plurality of projecting portions projecting from an outer circumferential surface thereof and provided along the longitudinal direction of the sensor; and the projecting portions of the separator coming into contact with an inner circumferential surface of the holder tube such that at least a portion of the separator is elastically deformed radially inward, whereby the separator elastically holds the sensor element and the terminal member within the holder tube.

In the liquid-condition detection sensor of the present invention, the separator having a plurality of projecting portions which come into contact with the inner circumferential surface of the holder tube is disposed within the holder tube, whereby the separator is elastically deformed inward via the plurality of projecting portions. This phenomenon of elastic deformation is utilized for elastically holding the sensor element and the terminal member by means of the separator.

This configuration allows the separator to elastically hold the sensor element and the terminal member within the holder tube, thereby eliminating the need for a step of deforming the holder tube so as to elastically deform the separator. Thus, the sensor element and the terminal member can be elastically held within the holder tube by means of a simple configuration and in a stable manner.

Preferably, in the above-mentioned liquid-condition detection sensor, the separator includes an inner-tube engagement portion projecting from the outer circumferential surface thereof and having an outside diameter greater than an inside diameter of the holder tube, and the inner-tube engagement portion of the separator engages a distal end of the holder tube.

In a configuration in which the separator holds at least either of the terminal member and the sensor element within the holder tube, application of tensile force of a certain magnitude to the electrically conductive path member connected to the terminal member in a direction opposite the terminal member may cause the separator to move within the holder tube. If the separator deviates from a proper position in relation to the holder tube, insulation between the terminal member and the holder tube may possibly be lost.

In order to cope with the above problem, in the liquid-condition detection sensor of the present invention, the separator has an inner-tube engagement portion whose outside diameter is greater than the inside diameter of the holder tube, and the inner-tube engagement portion engages a distal end of the holder tube. Accordingly, even when tensile force is applied to the electrically conductive path member connected to the terminal member, engagement of the inner-tube engagement portion with the distal end of the holder tube can prevent movement of the separator into the holder tube.

Preferably, in any one of the above-mentioned liquid-condition detection sensors, the sensor element is partially surrounded by the holder tube, and the separator includes an element abutment portion which abuts the sensor element and positions the sensor element within the separator along a proximal-end-distal-end direction.

In the liquid-condition detection sensor of the present invention, the separator has an element abutment portion for positioning the sensor element along the proximal-end-distal-end direction, which is a direction connecting the proximal and distal ends of the separator. Thus, merely by causing the proximal end or the distal end of the sensor element to abut the element abutment portion, the sensor element can be readily positioned within the separator along the proximal-end-distal-end direction.

Preferably, in any one of the above-mentioned liquid-condition detection sensors, the separator is formed from a material having rubberlike elasticity and has a through-hole wall portion through which a through hole extends for accommodating at least either of the electrically conductive path member and the terminal member. Furthermore, the through-hole wall portion has a slit which extends along the through hole from one end to the other end of the through hole and penetrates from an outer circumferential surface of the through-hole wall portion to the through hole. By opening the slit through deformation of the separator, at least either of the electrically conductive path member and the terminal member can be placed in the through hole through the slit.

The separator of the liquid-condition detection sensor of the present invention is formed from a material having rubberlike elasticity. This separator includes a through-hole wall portion, and the through-hole wall portion has a slit. By opening the slit through deformation of the separator, at least either of the electrically conductive path member and the terminal member can be placed in the through hole through the slit.

The above-described liquid-condition detection sensor eliminates the need to insert the electrically conductive path member into the through hole of the separator before the electrically conductive path member is connected to the terminal member of the sensor element, thereby facilitating its assembly. Also, in the case where the electrically conductive path member is previously inserted into the through hole of the separator, the shape of the separator and that of the through hole must be determined in consideration of movement of the electrically conductive path member and the terminal member associated with these members being pulled into the through hole. However, in the liquid-condition detection sensor of the present invention, the shape of the separator and that of the through hole can be determined without having to take these factors into consideration, so that the separator and the through hole can each assume such a shape as to be able to more appropriately hold the electrically conductive path member and the terminal member.

After at least either the electrically conductive path member and the terminal member is placed in the through hole through the opened slit, releasing the slit allows the through-hole wall portion to be deformed by its own elasticity so as to close the slit. Accordingly, this arrangement prevents the member from coming out of the through hole through the slit, thereby providing excellent reliability.

Preferably, in any one of the above-mentioned liquid-condition detection sensors, the sensor element comprises a first ceramic layer; a second ceramic layer superposed on the first ceramic layer; and a heat-generating resistor disposed between the first ceramic layer and the second ceramic layer and having a resistance which varies with the temperature of the resistor. When a voltage is applied to the heat-generating resistor or when a current is passed through the heat-generating resistor via the terminal member, the heat-generating resistor outputs an output signal indicative of a condition of the liquid to be measured.

In the liquid-condition detection sensor of the present invention, the sensor element has a heat-generating resistor whose resistance varies with temperature. The thermal capacity of liquid to be measured differs depending on the condition of liquid to be measured (specifically, the type of liquid to be measured, the concentration of a certain component contained in liquid to be measured, or the like). Thus, when a voltage is applied to the heat-generating resistor or when a current is passed through the heat-generating resistor having the above-mentioned property via the terminal member, a temperature variation (in other words, resistance variation) of the heat-generating resistor differs depending on the condition of a liquid to be measured. By use of the sensor element having the heat-generating resistor, the liquid-condition detection sensor of the present invention provides an output signal indicative of the condition of liquid to be measured from the heat-generating resistor. Therefore, the condition of liquid to be measured is readily detected.

The sensor element is configured such that the heat-generating resistor is disposed between the first ceramic layer and the second ceramic layer, whereby the sensor element can be brought into contact with liquid. Contact of the element with liquid improves accuracy in detecting the condition of liquid to be measured.

Examples of an "output signal" which the energized heat-generating resistor outputs in accordance with resistance thereof include a "voltage" signal which is developed across the resistor by passing a constant current through the heat-generating resistor, and a "current" signal upon application of a constant voltage to the heat-generating resistor.

Preferably, any one of the above-mentioned liquid-condition detection sensors further comprises an outer tube extending in the longitudinal direction of the sensor and radially surrounding the outside of the holder tube. The outer tube and the holder tube form a level sensor portion therebetween, forming a capacitor whose capacitance varies with the level of the liquid to be measured.

The liquid-condition detection sensor of the present invention has an outer tube which radially surrounds the outside of the holder tube, whereby the outer tube and the holder tube form a capacitance-operated level sensor portion therebetween. By configuring the liquid-condition detection sensor such that the capacitor-operated level sensor portion having excellent accuracy in detecting the level of liquid to be measured and the sensor element are united, a single sensor can accurately detect the condition of a liquid to be measured (e.g., detection of the type of liquid to be measured or detection of the concentration of a certain component contained in the liquid to be measured) by means of the sensor element as well as the level of liquid to be measured.

Preferably, in any one of the above-mentioned liquid-condition detection sensors, the liquid to be measured is a urea aqueous solution.

In the case where the liquid-condition detection sensor of the present invention is used in an exhaust gas purification apparatus mounted in an automobile or the like, even when this liquid-condition detection sensor is subjected to vibration or impact associated with driving or the like, continued use of the liquid-condition detection sensor is possible without incurring a short circuit or cracking.

BRIEF DESCRIPTION OF THE DRAWINGS

FIGS. 7(a) and 7(b) are views showing a separator for use in the liquid-condition detection sensor according to the present embodiment, wherein FIG. 7(a) is a perspective view, and FIG. 7(b) is a vertical sectional view.

DESCRIPTION OF REFERENCE NUMERALS

Figure 1:
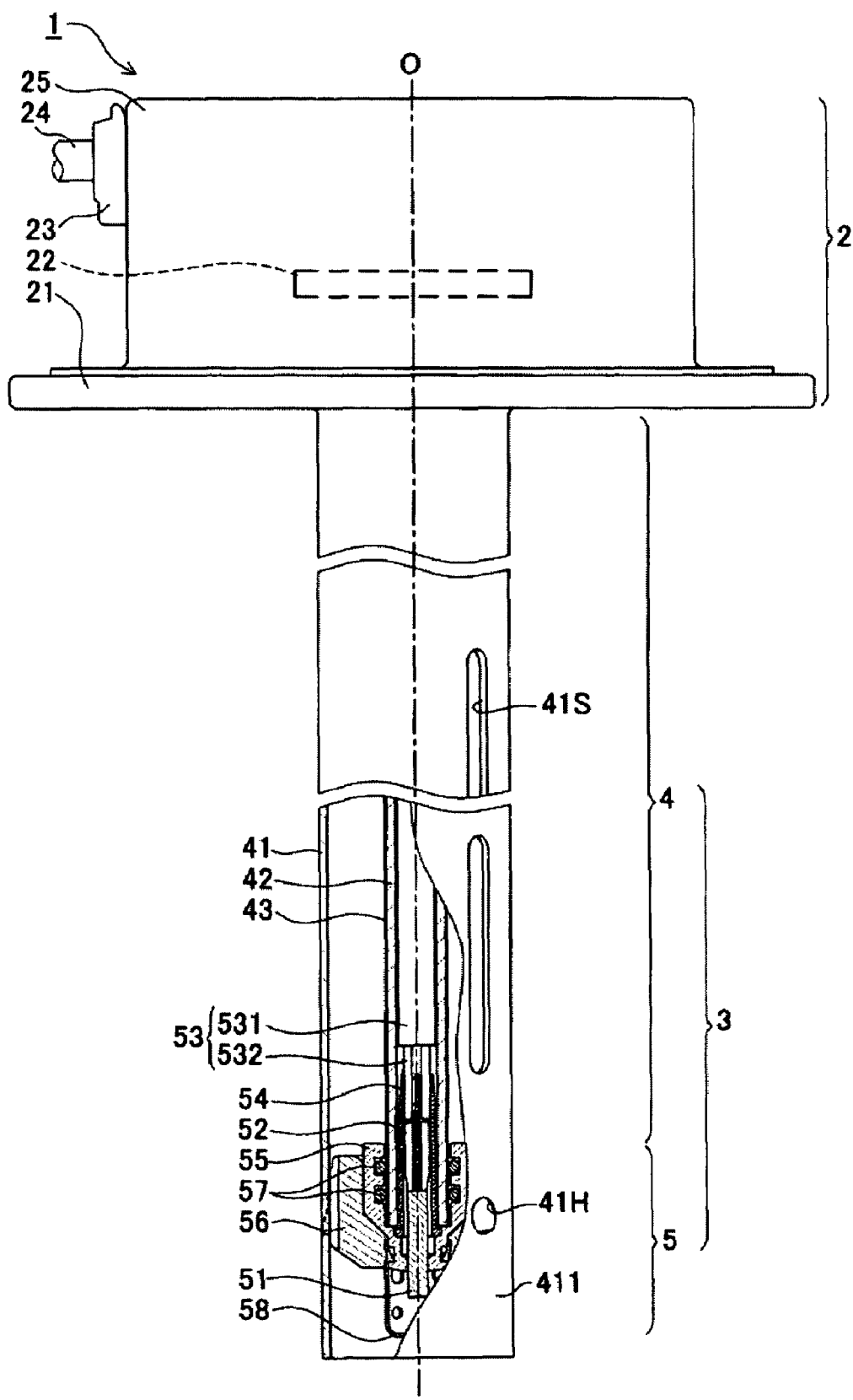
FIG. 1 is a partial cutaway, sectional view schematically showing a liquid-condition detection sensor according to an embodiment of the invention and the structure of essential portions of the sensor.

Reference numerals used to identify various structural features in the drawings include the following.
1: liquid-condition detection sensor
2: base section
22: wiring board
3: sensor section
4: liquid level sensor portion
41: outer tube
41H: retaining hole
42: inner tube (holder tube)
5: liquid concentration sensor portion
51: concentration sensor element
516: inner conductor (heat-generating resistor)
52: connection terminal (terminal member)
53: connection cable (electrically conductive path member)
532: lead wire
533: core
54: separator
54B: proximal end (of separator)
54C: distal end (of separator)
54H1, 54H2: through hole
54H3: hole communication portion
541: through-hole wall portion
541G: outer circumferential surface (of through-hole wall portion)
542: terminal-inner-tube-insulating portion (terminal-tube-insulating portion) (of through-hole wall portion)
544: terminal-holding portion
545: element-holding portion
546: inner-tube engagement portion
547: abutment projection (projecting portion)
548: inter-terminal insulating portion
549: element abutment portion (of inter-terminal insulating portion)
54S1, 54S2: slit
55: holder member
56: rubber bushing

DETAILED DESCRIPTION OF THE INVENTION

An embodiment of a liquid-condition detection sensor according to the present invention will be described with reference to the drawings. However, the present invention should not be considered as being limited thereto.

In the description of a liquid-condition detection sensor 1 according to the present embodiment as well as components thereof, the upper side along the direction of an axis O (axial direction) in FIG. 1 is called the proximal-end side, and the lower side is called the distal-end side.

The liquid-condition detection sensor 1 according to the present embodiment is used to detect, for example, the concentration and liquid level of a urea aqueous solution contained in a tank of an exhaust gas purification apparatus. The exhaust gas purification apparatus is used to render harmless nitrogen oxides (NOx) contained in exhaust gas from an automobile equipped with a diesel engine or the like by reducing the nitrogen oxides with the urea aqueous solution.

The liquid-condition detection sensor 1 includes a base section 2 and a sensor section 3 extending from the base section 2. In using the liquid-condition detection sensor 1, the base section 2 is attached to the periphery of an opening portion of a tank (not shown) containing the urea aqueous solution, and the sensor section 3 provided on the distal-end side of the base section 2 is immersed in the urea aqueous solution.

In the liquid-condition detection sensor 1, the base section 2 includes a mounting flange portion 21, a cover 25, a wiring board 22 covered with the mounting flange portion 21 and the cover 25, an external connection cable 24, and a bushing 23 for holding the external connection cable 24. The sensor section 3 includes a liquid level sensor portion 4 in the form of a dual cylinder and a liquid concentration sensor portion 5 located at a distal end portion of the liquid level sensor portion 4.

First, the base section 2 will be described. The mounting flange 21 is formed from metal, is located at the distal end of the base section 2, and is used as a pedestal for mounting the liquid-condition detection sensor 1 to the periphery of an opening portion of a tank (not shown). The mounting flange 21 has unillustrated bolt holes for fixedly attaching the liquid-condition detection sensor 1 to the tank with bolts.

The wiring board 22 is provided on the proximal-end side of the mounting flange 21. A control circuit having a CPU, electric circuits, and the like is formed on the wiring board 22. The control circuit is electrically connected to the liquid level sensor portion 4 and the liquid concentration sensor portion 5, and can be connected to an external electric circuit (e.g., ECU) via the external connection cable 24. The wiring board 22 is covered with the cover 25 attached to the mounting flange portion 21 to protect the same.

Figure 6:
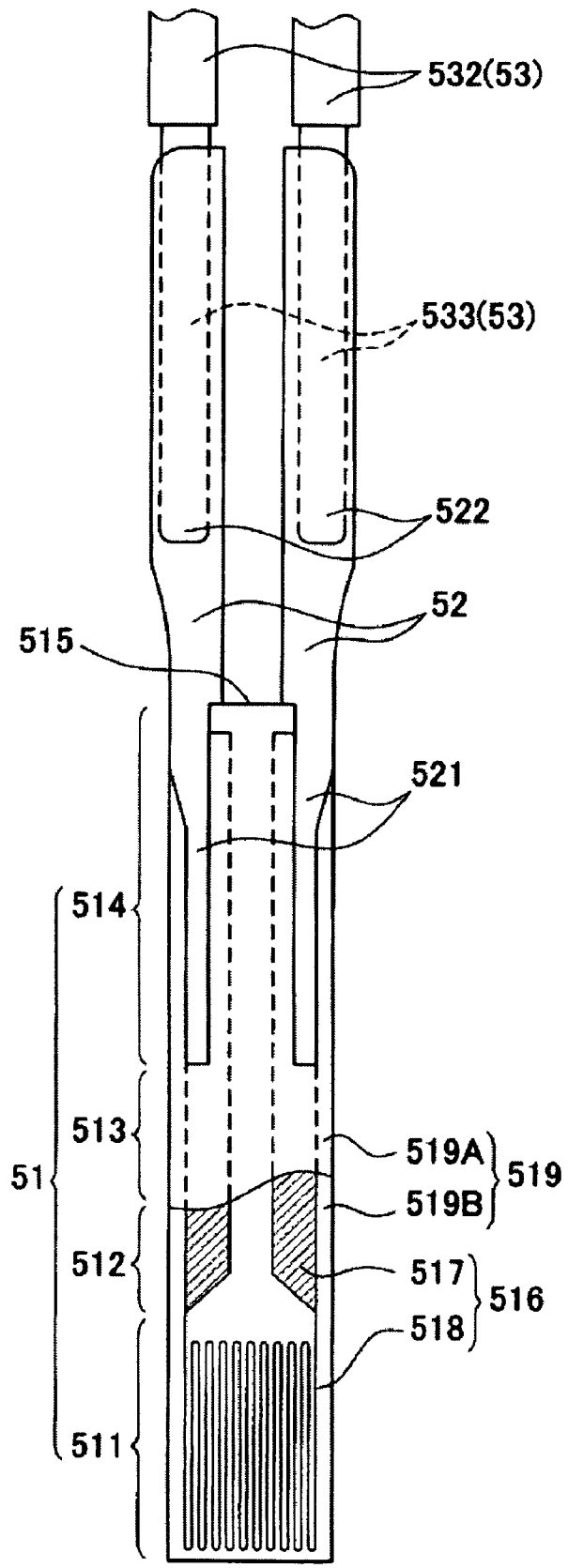
FIG. 6 is an explanatory view showing a sensor element, connection terminals, and lead wires for use in the liquid-condition detection sensor according to the present embodiment and showing their connections.

The control circuit formed on the wiring board 22 detects the concentration of the urea aqueous solution on the basis of an output signal which is output from a concentration sensor element 51 of the liquid concentration sensor portion 5 shown in FIG. 6. The output signal results from energizing the sensor element 51 and corresponds to the resistance of an inner heater wire 518. The output signal, for example, is a voltage developed across the concentration sensor element 51 by passing a predetermined current therethrough.

Next, the sensor section 3 will be described. As mentioned above, the sensor section 3 includes the liquid level sensor portion 4 and the liquid concentration sensor portion 5. First, the liquid level sensor portion 4 will be described, and then the liquid concentration sensor portion 5 will be described.

As shown in FIG. 1, the liquid level sensor portion 4 includes an outer tube 41 having a cylindrical shape and extending along the axis O (longitudinal direction) and an inner tube 42, which is disposed within the outer tube 41. The inner tube 42 extends in the longitudinal direction coaxially with the outer tube 41, and has a cylindrical shape having a diameter smaller than that of the outer tube 41. The inner circumferential surface of the outer tube 41 and the outer circumferential surface of the inner tube 42 are spaced a predetermined distance apart from one another. The inner tube 42 corresponds to the holder tube of the present invention.

The outer tube 41 is formed from metal and serves as one of two electrodes for detecting a liquid level. The outer tube 41 has a plurality of narrow slits 41S extending along the axis O and located at predetermined positions, whereby the urea aqueous solution can be accommodated in a space between the outer tube 41 and the inner tube 42 while communicating with the exterior of the outer tube 41. The distal end (the lower end in FIG. 1) of the outer tube 41 is open, and the proximal end of the outer tube 41 is fixedly attached to the mounting flange 21 by welding or the like. In the present embodiment, the outer tube 41 is welded to the mounting flange 21. Furthermore, the mounting flange 21 is connected to the ground potential of the control circuit formed on the wiring board 22, whereby the outer tube 41 is grounded.

Figure 2:
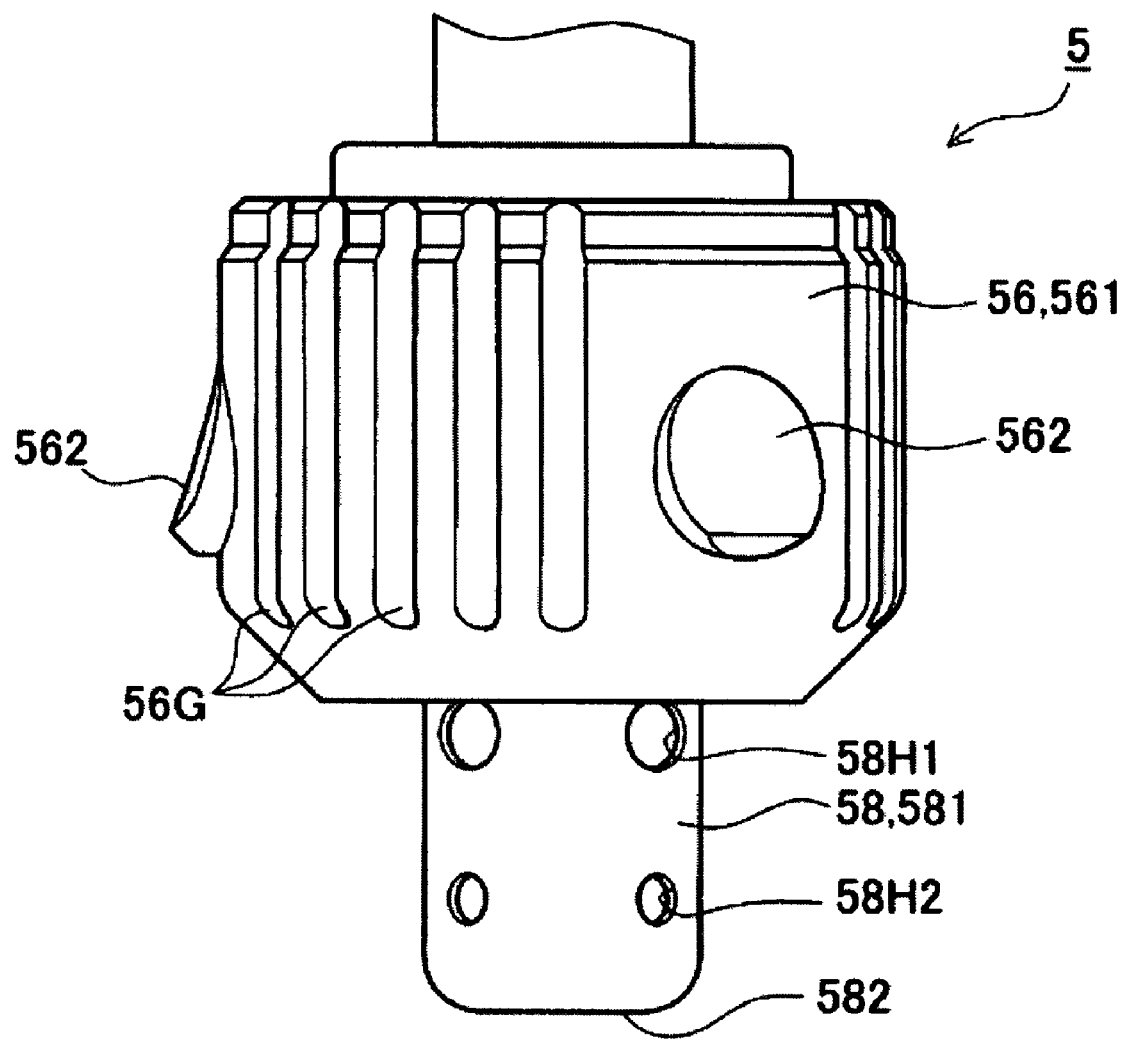
FIG. 2 is a fragmentary, enlarged side view of a liquid concentration sensor portion as viewed in a state in which an outer tube is removed from the liquid-condition detection sensor according to the present embodiment.

A rubber bushing 56, which will be described later, intervenes between a distal end portion 411 of the outer tube 41 and a distal end portion 421 of the inner tube 42 (see FIG. 4). The outer tube 41 has a plurality of retaining holes 41H which are circumferentially arranged at predetermined positions (see FIG. 1). The retaining holes 41H engage respective engagement projections 562 of the rubber bushing 56 (see FIG. 2), thereby retaining the rubber bushing 56 (liquid concentration sensor portion 5).

The inner tube 42 is also formed from metal and serves as the other electrode for detecting a liquid level. While being electrically insulated from the outer tube 41, the inner tube 42 faces the outer tube 41 and is electrically connected to the control circuit on the wiring board 22. An insulating film 43 of, for example, a fluorine-containing resin such as PTFE or PFA, an epoxy resin, or a polyimide resin is formed on an outer circumferential surface 42G of the inner tube 42 (see FIG. 4), thereby insulating the inner tube 42 and the outer tube 41 from each other even though the conductive urea aqueous solution (liquid to be measure) is present therebetween.

The liquid level sensor portion 4 detects the liquid level of the urea aqueous solution as follows. The liquid level sensor portion 4 is immersed in the urea aqueous solution so as to introduce the urea aqueous solution into a space between the outer tube 41 and the inner tube 42 (electrically insulative film 43) through the slits 41S.

In the liquid level sensor portion 4, the space between the outer tube 41 and the inner tube 42 is divided into a region where the urea aqueous solution is present, and a region where the urea aqueous solution is absent, in accordance with the urea liquid level. Thus, the capacitance of a capacitor formed between the outer tube 41 and the inner tube 42 varies with the urea liquid level. When an AC voltage is applied between the outer tube 41 and the inner tube 42, a current corresponding to the magnitude of this capacitance flows; therefore, the liquid level of the urea aqueous solution can be detected on the basis of the magnitude of the current or flow.

Next, the liquid concentration sensor portion 5 will be described.

Figure 4:
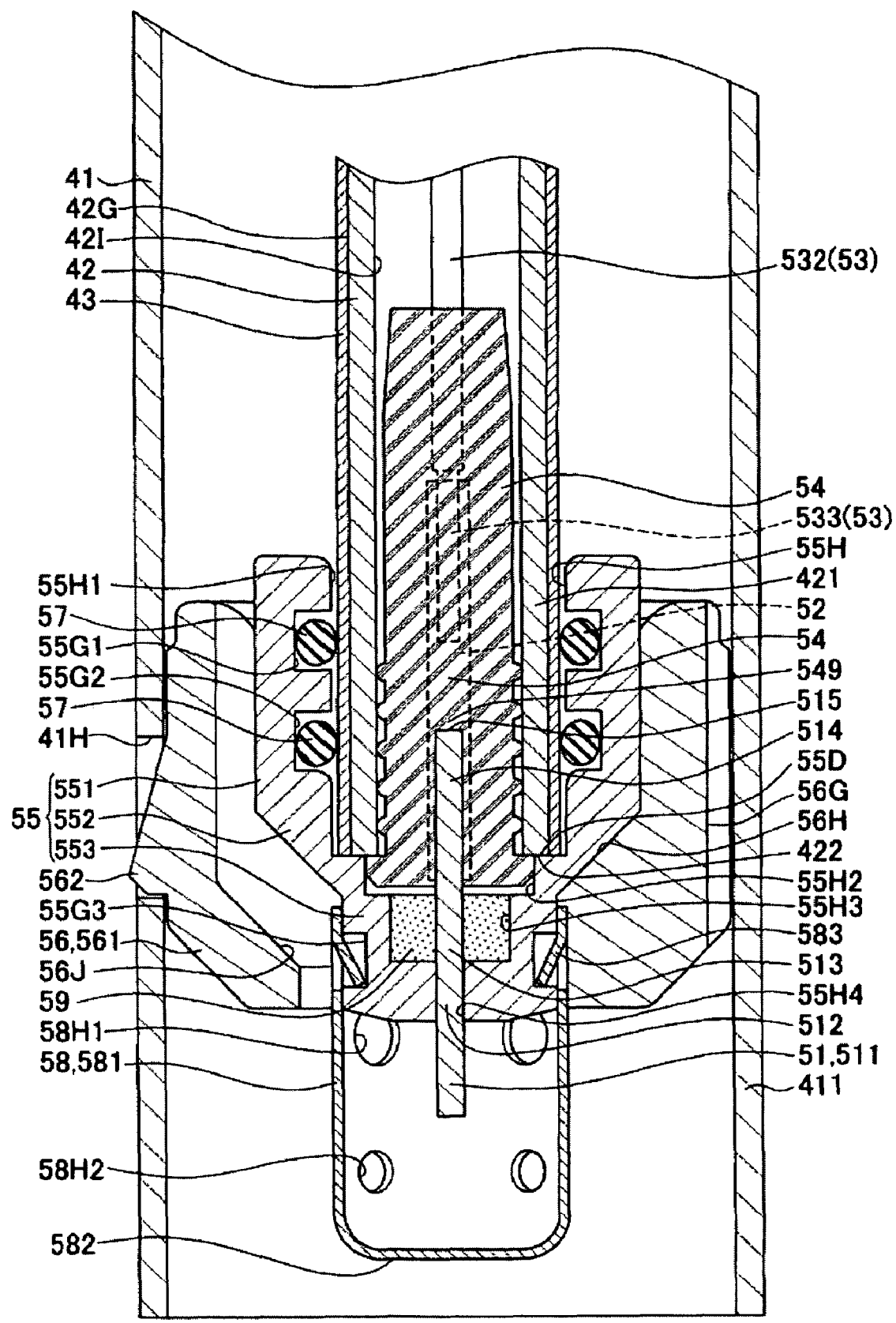
FIG. 4 is a vertical sectional view taken along line A-A' of FIG. 3, showing the liquid concentration sensor portion of the liquid-condition detection sensor according to the present embodiment.
Figure 5:
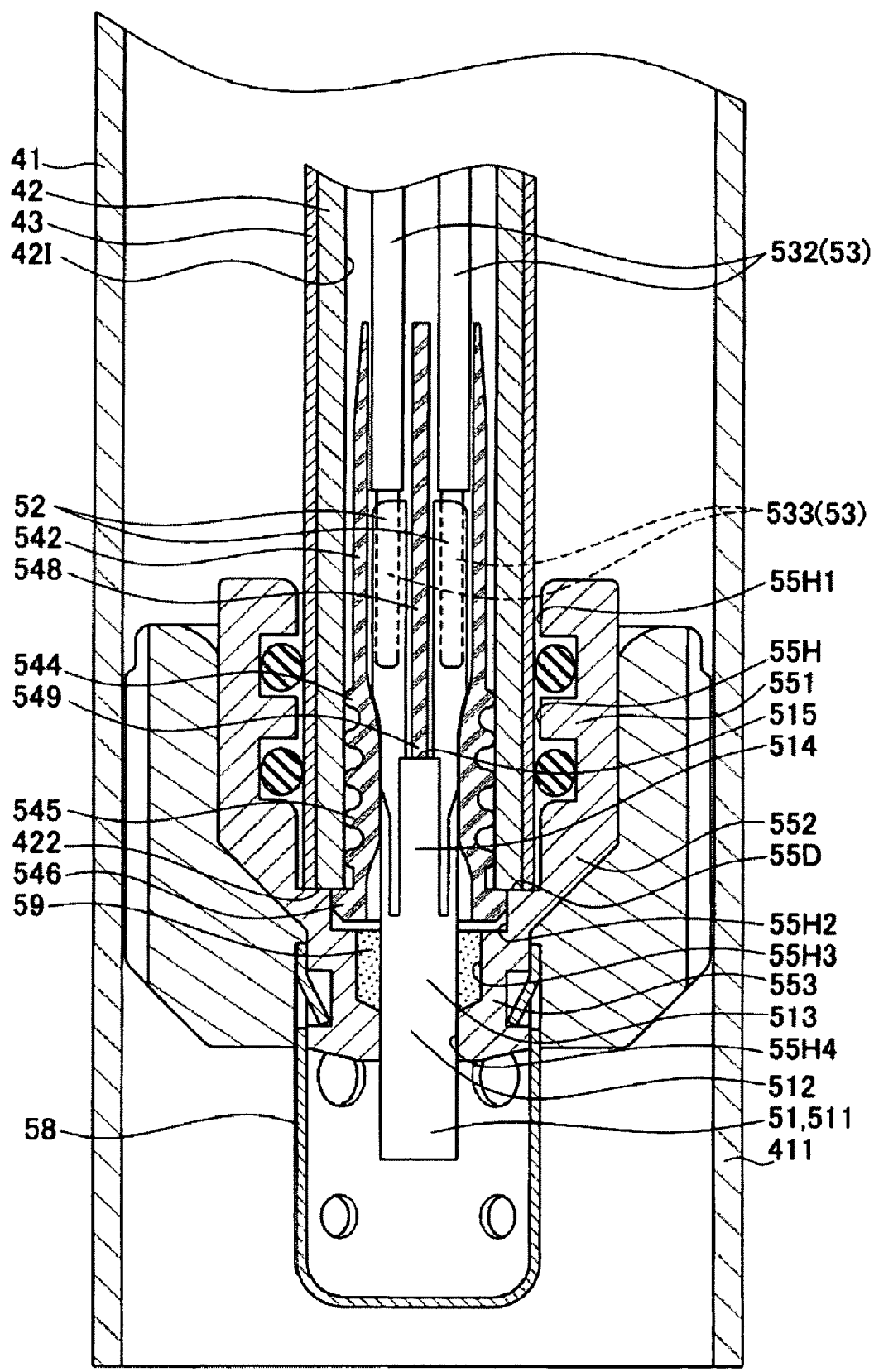
FIG. 5 is a partial cutaway, vertical sectional view taken along line B-B' of FIG. 3, showing the liquid concentration sensor portion of the liquid-condition detection sensor according to the present embodiment.

The liquid concentration sensor portion 5 is located on the distal-end side of the liquid level sensor portion 4 and includes the concentration sensor element 51, a holder member 55, a protector 58, and the rubber bushing 56 (see FIGS. 1, 4, and 5).

The concentration sensor element 51 is held in the interior of the holder member 55. The concentration sensor element 51 is electrically connected to the control circuit formed on the wiring board 22 via connection terminals 52 soldered thereto and a connection cable 53. The holder member 55 is held at the distal end portion 411 of the outer tube 41 by means of the rubber bushing 56 surrounding the same and intervening between the same and the outer tube 41. The protector 58 engages with and is held by a distal end portion (small-diameter portion 553) of the holder member 55.

First, among the components of the liquid concentration sensor portion 5, the concentration sensor element 51 (see FIG. 6) will be described. The concentration sensor element 51 assumes the form of a rectangular sheet as viewed in plane and includes a flat-sheet-like two-layered ceramic layer 519 (519A and 519B) formed from alumina ceramic, and an inner conductor 516 liquid-tightly disposed between the ceramic layers 519A and 519B. The inner conductor 516 includes a pair of wide inner leads 517 and the inner heater wire 518, which zigzags in the form of bellows between the paired inner leads 517.

The concentration sensor element 51 is divided into a distal end portion 511 in which the inner heater wire 518 is disposed, an insertion portion 512 which is adjacent to the proximal-end side (upper side in FIG. 6) of the distal end portion 511, a resin retainment portion 513 located on the proximal-end side of the insertion portion 512, and a proximal end portion 514 to which the paired connection terminals 52 are connected by soldering.

Each of the connection terminals 52 is formed by bending a metal sheet having a predetermined shape into a shape having a cross section resembling a squared letter U. A distal end portion 521 each of the connection terminals 52 extends toward the distal-end side (downward in FIG. 6) and is connected by soldering to an unillustrated pad formed on the proximal end portion 514 of the concentration sensor element 51, thereby being fixedly attached to the concentration sensor element 51. By this procedure, the connection terminal 52 (distal end portion 521) is connected to the corresponding inner lead 517 by means an unillustrated via conductor extending through the ceramic layer 519A. Thus, when voltage is applied between the paired connection terminals 52, mainly the inner heater wire 518 generates heat by energizing the inner heater wire 518 through the inner leads 517. The inner conductor 516 including the inner heater wire 518 is formed from a material whose resistance varies with its temperature, such as platinum or tungsten, and corresponds to the heat-generating resistor of the present invention.

Cores 533 of lead wires 532 of the connection cable 53 are electrically and mechanically connected by soldering to respective proximal end portions 522 of the connection terminals 52. As shown in FIG. 1, the connection cable 53 extends through the inner tube 42 toward the proximal-end side (upward in FIG. 1) and is connected to the wiring board 22 (control circuit). That is, the inner tube 42 surrounds a portion (most) of the connection cable 53.

Next, the holder member 55 will be described. The holder member 55 is formed from an electrically insulative resin material. As shown in FIGS. 4 and 5, the holder member 55 includes a cylindrical large-diameter portion 551 having a relatively large diameter, a cylindrical small-diameter portion 553 smaller in diameter than the large-diameter portion 551, and a taper portion 552 located between the large-diameter portion 551 and the small-diameter portion 553 and having a tapered outer circumferential surface. The holder member 55 is a hollow member having a holder through-hole 55H which extends therethrough in the axial direction. The holder through-hole 55H includes an inner-tube-holding portion 55H1, a second stepped portion 55H2, and a third stepped portion 55H3, which gradually reduce in diameter from the proximal-end side, as well as an element-holding portion 55H4 located farthest on the distal-end side and having a substantially rectangular cross section.

As shown in FIGS. 4 and 5, the holder member 55 holds the concentration sensor element 51. Specifically, the insertion portion 512 of the concentration sensor element 51 is inserted into the element-holding portion 55H4 of the holder member 55, and the resin retainment portion 513 of the concentration sensor element 51 disposed within the third stepped portion 55H3 is fixed in place by means of a sealing resin 59 which fills the third stepped portion 55H3. The sealing resin 59 provides a liquid-tight seal between the concentration sensor element 51 and the holder member 55.

Thus, the concentration sensor element 51 is disposed such that the distal end portion 511, in which the inner heater wire 518 is disposed, projects toward the distal-end side (downward in FIG. 1) from the holder member 55.

The holder member 55 holds the distal end portion 421 of the inner tube 42 in the inner-tube-holding portion 55H1 of the holder through-hole 55H. A distal end 422 of the inner tube 42 buts an inner-tube abutment face 55D located between the inner-tube-holding portion 55H1 and the second stepped portion 55H2, whereby the inner tube 42 and the holder member 55 are axially positioned relative to one another. Two ring grooves 55G1 and 55G2 are formed in the inner-tube-holding portion 55H1 of the holder through-hole 55H. O-rings 57 disposed in the respective ring grooves 55G1 and 55G2 provide a liquid-tight seal between the holder member 55 and the inner tube 42 (electrically insulative film 43).

Since the holder member 55, which holds the concentration sensor element 51, and the inner tube 42 are connected together as mentioned above, most of the proximal end portion 514 of the concentration sensor element 51 and the entirety of the connection terminals 52 are disposed within the inner tube 42. In the present embodiment, the distal end portion 421 of the inner tube 42 indirectly holds the concentration sensor element 51 via the holder member 55. Furthermore, a separator 54 is disposed within the inner tube 42 while insulating the concentration sensor element 51 and the connection terminals 52 from the inner tube 42.

Next, the separator 54 will be described with reference to FIGS. 7(a) and 7(b).

The separator 54 is formed from an electrically insulative resin having rubberlike elasticity and assumes a substantially columnar form. The separator 54 has a through-hole wall portion 541 through which two through holes 54H1 and 54H2 extend in the axial direction in parallel with each other, and a wall-like inter-terminal insulating portion 548 which separates the two through holes 54H1 and 54H2 from each other. As shown in FIGS. 4 and 5, the two through holes 54H1 and 54H2 allow insertion and retention of the respective connection terminals 52 and lead wires 532 therein.

Distal end portions of the two through holes 54H1 and 54H2 communicate with each other through a hole communication portion 54H3. The hole communication portion 54H3 and those portions of the through holes 54H1 and 54H2 which communicate with each other through the hole communication portion 54H3 receive the inserted proximal end portion 514 of the concentration sensor element 51. Accordingly, by means of a proximal end 515 of the concentration sensor element 51 abutting a distal-end element abutment portion 549 of the inter-terminal insulating portion 548, which separates the two through holes 54H1 and 54H2 from each other, the concentration sensor element 51 can be positioned within the separator 54 in the proximal-end-distal-end direction, which connects the proximal end and the distal end of the separator 54; i.e., in the axial direction (see FIG. 5).

A distal end portion of an outer circumferential surface 541G of the separator 54 (through-hole wall portion 541) has a plurality of (five in the present embodiment) ring-like abutment projections 547 arranged along the axis O. When the separator 54 is inserted into the inner cylinder 42, the abutment projections 547 abut an inner circumferential surface 421 of the inner tube 42 and cause the through-hole wall portion 541 (separator 54) to be deformed radially inward.

Furthermore, a distal end portion of the separator 54 is formed into an inner-tube engagement portion 546 which projects radially outward, is engaged with the distal end 422 of the inner tube 42, and limits the depth of insertion of the separator 54 into the inner tube 42 (see FIG. 5). As will be described below, in the present embodiment, since the separator 54 partially holds the connection terminals 52 and the concentration sensor element 51, subjecting the connection cable 53 to tensile force may possibly cause the separator 54 to be pulled into the inner tube 42. However, engagement of the inner-tube engagement portion 546 of the separator 54 with the distal end of the inner tube 42 can prevent the separator 54 from being pulled into the inner tube 42 even when a tensile force is applied to the connection cable 53.

The separator 54 is inserted into the distal end portion 421 of the inner tube 42 in the following state: the concentration sensor element 51 is inserted into the hole communication portion 54H3 and into those portions of the through holes 54H1 and 54H2 which communicate with one another through the hole communication portion 54H3; the proximal end 515 of the concentration sensor element 51 abuts the element abutment portion 549; and the connection terminals 52 and the lead wires 532 are disposed in the respective through holes 54H1 and 54H2.

In the present embodiment, the through-hole wall portion 541 of the separator 54 intervenes between the inner tube 42 and the connection terminals 52 (see FIGS. 4 and 5). Specifically, a terminal-inner-tube-insulating portion 542 (see FIG. 7b), which is an axially central portion of the separator 54 (through-hole wall portion 541), intervenes between the inner tube 42 and the connection terminals 52. This reliably prevents contact and a resultant short circuit between the connection terminals 52 and the inner tube 42.

The inter-terminal insulating portion 548 of the separator 54 intervenes between the paired connection terminals 52. This reliably prevents contact and a resultant short circuit between the connection terminals 52.

Furthermore, as mentioned above, the separator 54 has the abutment projections 547 at a distal end portion thereof. Thus, when the separator 54 is inserted into the inner tube 42, a deformation portion 543 of the through-hole wall portion 541 where the abutment projections 547 are formed is deformed radially inward.

Before the separator 54 is inserted into the inner tube 42, the concentration sensor element 51, the connection terminals 52, and the lead wires 532 are loosely inserted into the two through holes 54H1 and 54H2 of the separator 54.

However, when the separator 54 is inserted into the inner tube 42, the abutment projections 547 abut the inner circumferential surface 421 of the inner tube 42, whereby the through-hole wall portion 541 (deformation portion 543) is deformed radially inward. Thus, as shown in FIG. 5, a terminal-holding portion 544 of the deformation portion 543 of the through-hole wall portion 541 comes into elastic contact with the connection terminals 52, thereby holding the connection terminals 52. Therefore, even when the liquid-condition detection sensor 1 is subjected to vibration or impact as in the case of the same being mounted in an automobile or the like, since the terminal-holding portion 544 elastically holds the connection terminals 52, vibration of the connection terminals 52 is suppressed.

Similarly, an element-holding portion 545 of the deformation portion 543 of the through-hole wall portion 541 comes into elastic contact with the concentration sensor element 51, thereby holding the concentration sensor element 51. Thus, even when subjected to vibration or impact, since the element-holding portion 545 elastically holds the concentration sensor element 51, vibration of the concentration sensor element 51 is suppressed.

Accordingly, the occurrence of cracking or a like problem can be prevented in connections between the connection terminals 52 and the respective lead wires 532 which are made by soldering or the like, in connections between the connection terminals 52 and the concentration sensor element 51, and in portions of the connection terminals 52 and the concentration sensor element 51 in the vicinity of the connections, which could otherwise result from vibration of the connection terminals 52 and the concentration sensor element 51.

Figure 7A:
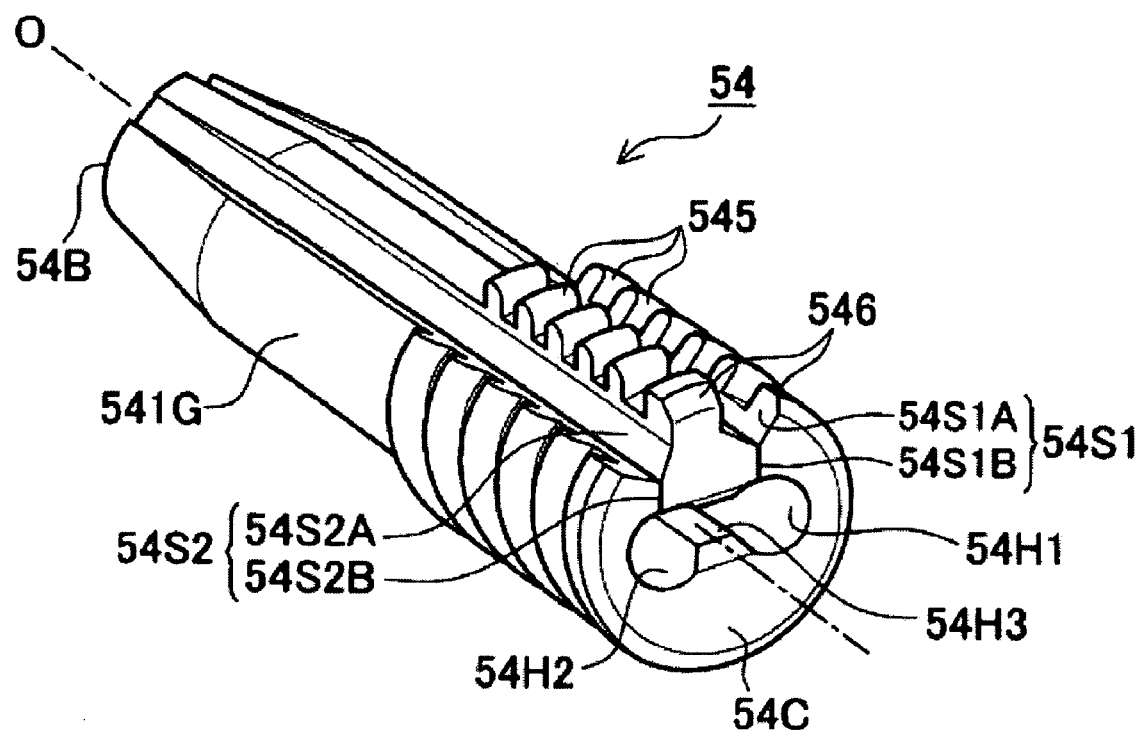
Figure 7B:
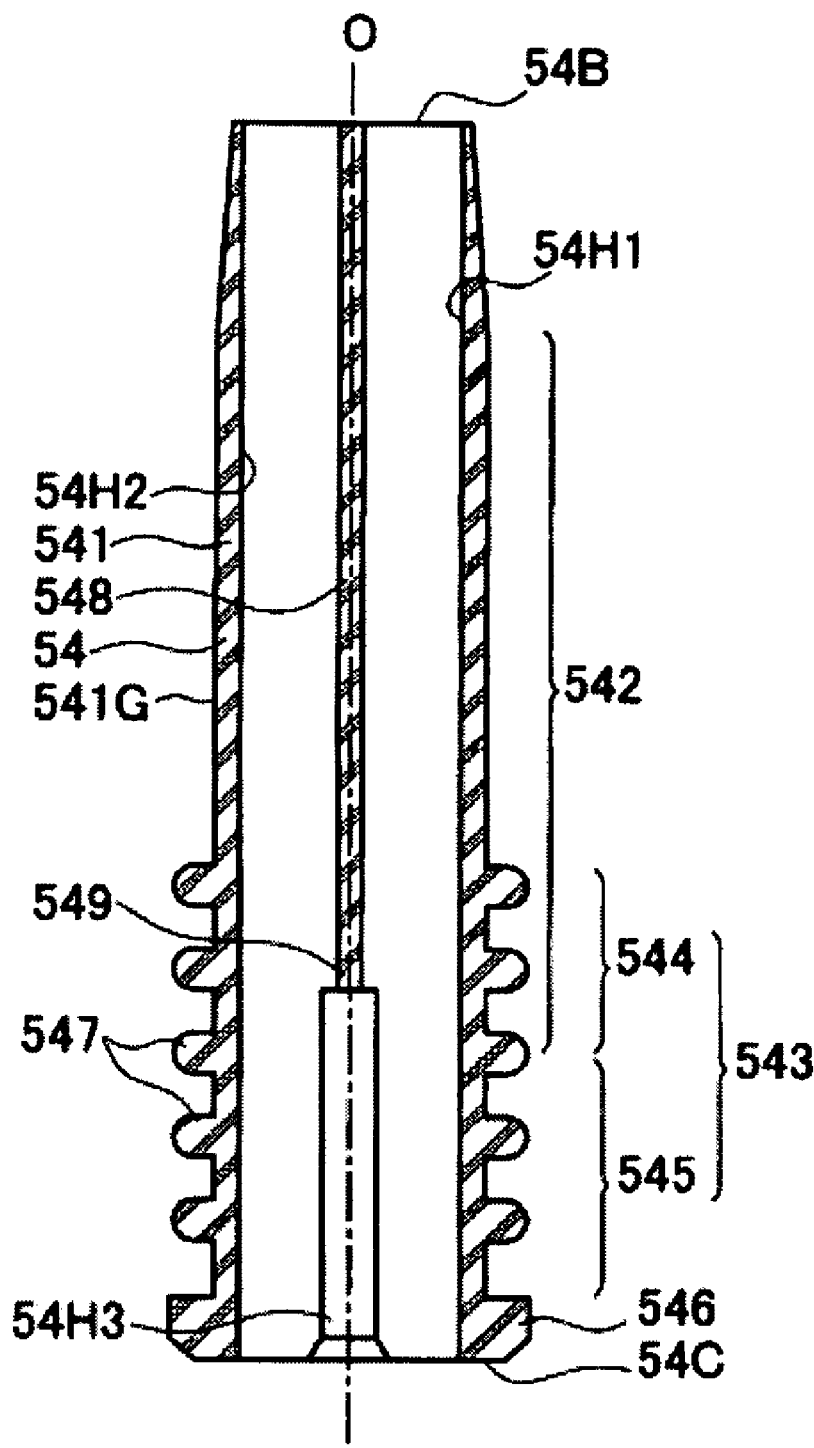

As shown in FIG. 7(a), the separator 54 in the present embodiment has slits 54S1 and 54S2 which penetrate the through-hole wall portion 541 from the outer circumferential surface 541G to the two through holes 54H1 and 54H2. The slits 54S1 and 54S2 include outer V-shaped groove portions 54S1A and 54S2A having a V-shaped cross section and cut-like slit portions 54S1B and 54S2B, respectively, and extend along the through holes 54H1 and 54H2, respectively, from one end to the other end thereof (from a proximal end 54B to a distal end 54C of the separator 54). Forming the slits 54S1 and 54S2 for the two through holes 54H1 and 54H2, respectively, facilitates disposition of the concentration sensor element 51, the connection terminals 52, and the lead wires 532 (cores 533) in the through holes 54H1 and 54H2. Specifically, the separator 54 is used as follows. First, the connection terminals 52 are connected to the concentration sensor element 51, and the lead wires 532 (cores 533) are connected to the respective connection terminals 52. Subsequently, the separator 54 is deformed so as to open the slits 54S1 and 54S2. The concentration sensor element 51, the connection terminals 52, and the lead wires 532 (cores 533) are disposed in the corresponding through holes 54H1 and 54H2 through the opened slits 54S1 and 54S2. This eliminates the need to previously insert the lead wires 532 into the respective through holes 54H1 and 54H2. Furthermore, in the present embodiment, even when only the lead wires 532 extending from a cable portion 531 of the connection cable 53 are shortened, the lead wires 532 can be connected to the respective connection terminals 52. This eliminates excess portions of the lead wires 532 after assembly and facilitates assembly.

Next, the protector 58 of the liquid concentration sensor portion will be described.

As shown in FIGS. 2 to 5, the protector 58 includes a cylindrical side portion 581 and a bottom portion 582, which closes the distal end of the side portion 581. The protector 58 assumes the form of a cap resembling a closed-bottomed cylinder. The side portion 581 and the bottom portion 582 have liquid communication holes 58H1, 58H2, and 58H3 for allowing the urea aqueous solution to flow between the interior and the exterior of the protector 58. The side portion 581 has latch tongues 583 in the vicinity of its proximal end. The latch tongues 583 are formed by making respective cuts each resembling a square letter U in the side portion 581 and bending the cut portions radially inward.

The protector 58 is disposed so as to surround the small-diameter portion 553 of the holder member 55 and the distal end portion 511 of the concentration sensor element 51 by latching the latch tongues 583 in respective protector latch groove 55G3 formed on the outer circumferential surface of the small-diameter portion 553 of the holder member 55.

The holder member 55 which holds the concentration sensor element 51 and the protector 58 as mentioned above is held by the rubber bushing 56 having a holder-holding hole 56H whose shape fits the geometry of the holder member 55.

The rubber bushing 56 is formed from an electrically insulative, high polymeric material having rubberlike elasticity. As shown in FIGS. 2 to 5, the rubber bushing 56 has a cylindrical bushing body portion 561 through which the holder-holding hole 56H coaxially extends and which bushing body portion 561 has an outside diameter allowing the same to fit into the outer tube 41, and three latch projections 562 which are formed on the outer circumferential surface of the bush body portion 561 while being equally spaced in the circumferential direction and which project radially outward from the bushing body portion 561. The holder-holding hole 56H of the bush body portion 561 is shaped so as to be able to hold the holder member 55 and the protector 58 through close contact therewith.

Figure 3:
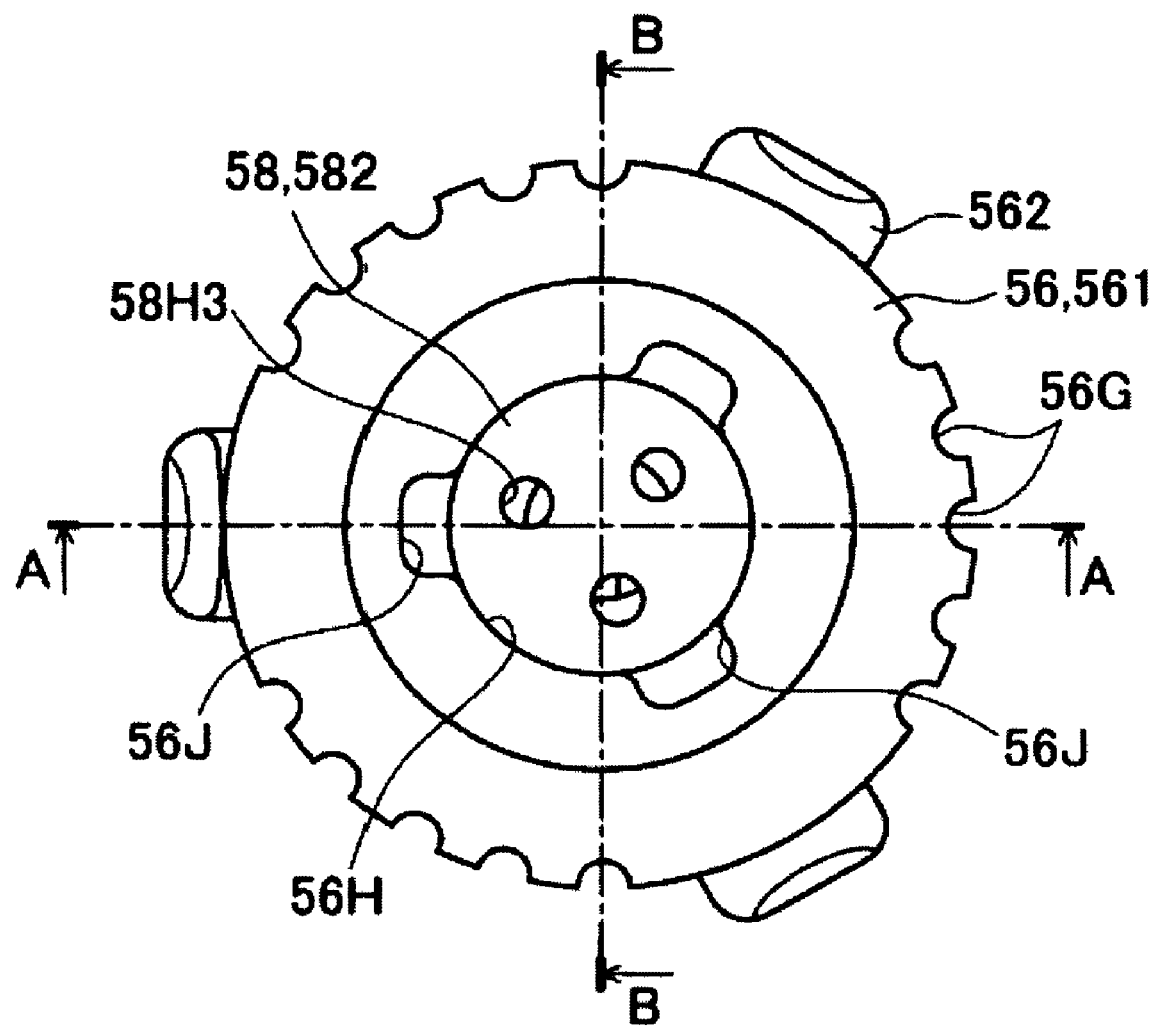
FIG. 3 is a fragmentary, enlarged bottom view of the liquid concentration sensor portion as viewed in a state in which the outer tube is removed from the liquid-condition detection sensor according to the present embodiment.

As will be readily understood from FIGS. 3 and 4, three axially extending inner slits 56J are formed on the wall surface of the holder-holding hole 56H. Also, a large number of axially extending outer slits 56G are formed on the outer circumferential surface of the rubber bushing 56 (bushing body portion 561) in regions between the latch projections 562 (see FIGS. 2 and 3). The inner slits 56J and the outer slits 56G serve as flow grooves allowing flow of the urea aqueous solution between the proximal-end side and the distal-end side of the rubber bushing 56. The protector 58 is held in the outer tube 41 by latching the latch projections 562 in the respective retaining holes 41H of the outer tube 41. Thus, the holder member 55 which holds the concentration sensor element 51 and the protector 58 is held by the rubber bushing 56 which in turn is held by the outer tube 41, whereby the entire liquid concentration sensor portion 5 is held between the distal end portion 411 of the outer tube 41 and the distal end portion 421 of the inner tube 42.

Next operation of the liquid concentration sensor portion 5 in the present embodiment will be described for detecting the urea concentration of the urea aqueous solution.

In the liquid-condition detection sensor 1 of the present embodiment, the control circuit formed on the wiring board 22 passes a constant current through the concentration sensor element 51 of the liquid concentration sensor portion 5, thereby causing the inner heater wire 518 to generate heat. By this procedure, a detection voltage corresponding to the magnitude of resistance of the inner heater wire 518 is developed across the inner heater wire 518. The control circuit detects variations in this detection voltage, thereby detecting the concentration of urea contained in the urea aqueous solution. Specifically, the detection voltage is measured immediately or rather just after start of application of electricity to the concentration sensor element 51 and after a predetermined period of time has passed from the start of application of electricity. The urea concentration of the urea aqueous solution corresponding to the change in detection voltage during the predetermined time period is obtained from a previously determined relationship between the urea concentration of the urea aqueous solution and the change in detection voltage.

In the present embodiment, the urea concentration of the urea aqueous solution is detected by use of the CPU and the like of the control circuit. The control circuit outputs a signal indicative of concentration information to an external circuit (e.g., ECU) through the external connection cable 24. On the basis of the input signal indicative of concentration information, the external circuit judges whether or not the concentration of the urea aqueous solution is within a specified range. When the external circuit judges that the concentration falls outside the specified range or that a liquid other than the urea aqueous solution is mixed in the urea aqueous solution, the external circuit notifies a vehicle driver of the fault or performs a like appropriate process.

While the present invention has been described with reference to the above embodiment, the present invention is not limited thereto, but may be modified as appropriate without departing from the spirit and scope of the claims appended hereto.

For example, the above embodiment is described in reference to the liquid-condition detection sensor 1 in which the liquid-level sensor portion 4 and the liquid concentration sensor portion 5 are united. However, the present invention is also applicable to a liquid-condition detection sensor which does not have a liquid level sensor function or which does not have an outer tube. The above embodiment is described in reference to a method of detecting the urea concentration of the urea aqueous solution at the liquid concentration sensor portion 5. However, the temperature of the urea aqueous solution can be determined from a resistance measurement taken just after start of application of electricity to the concentration sensor element 51 (inner heater wire 518). Thus, the liquid-condition detection sensor can be used as a liquid temperature sensor for measuring the temperature of the urea aqueous solution in addition to a sensor for detecting the urea concentration of the urea aqueous solution.

The above embodiment is described in reference to the separator 54 which has an inter-terminal insulating portion 548 for insulating the two parallel connection terminals 52 from each other. However, in the case where the connection terminals 52 do not need to be insulated from one another, the inter-terminal insulation portion 548 can be eliminated. In the case where a large number of connection terminals must be used, an inter-terminal insulating portion of a more complicated structure or a plurality of inter-terminal insulating portions can be provided.

In the above-described embodiment, not only the connection terminals 52 but also the proximal end portion 514 of the concentration sensor element 51 is disposed within the separator 54. However, if insulation is required only between the connection terminals and the inner tube and between the connection terminals, the present invention can be embodied such that the concentration sensor element 51 is not disposed within the separator 54.

The above embodiment is described in reference to the separator 54 which has five abutment projections 547 for deforming the through-hole wall portion 541 (deformation portion 543) radially inward. However, the abutment projections may be designed appropriately in terms of quantity, arrangement, form, and the like. If elastic holding of the connection terminals is not required while insulation between the connection terminals and the inner tube and between the connection terminals is taken into consideration, the present invention can be embodied such that the abutment projections are not present.

According to the liquid-condition detection sensor 1 of the above-described embodiment, the separator 54 is configured as follows. Before the separator 54 is inserted into the inner tube 42, the concentration sensor element 51, the connection terminals 52, and the lead wires 532 are loosely inserted into the two through holes 54H1 and 54H2 of the separator 54. When the separator 54 is inserted into the inner tube 42, the through-hole wall portion 541 (deformation portion 543) is deformed radially inward, thereby elastically holding the connection terminals 52 and the concentration sensor element 51. However, the liquid-condition detection sensor may be embodied while having a separator configured such that, through reduction of the diameter of the through holes or provision of projections projecting into the interior of the through holes, the through-hole wall portion of the separator elastically holds the connection terminals or the concentration sensor element in the through holes from a time before the separator is inserted into the inner tube.

In the above-described embodiment, the proximal end 515 of the concentration sensor element 51 is caused to abut the element abutment portion 549 located at the distal end of the inter-terminal insulating portion 548 of the separator 54, thereby positioning the concentration sensor element 51. However, a different portion of the concentration sensor element may abut another portion of the separator for positioning the concentration sensor element. The liquid-condition detection sensor 1 of the above-described embodiment has a wiring board 22 on which the control circuit is mounted. However, no particular limitation is imposed on the liquid-condition detection sensor of the present invention so long as a sensor element, such as the concentration sensor element 51, and an electrically conductive path member electrically communicating with the sensor element, such as the cable, are provided. Thus, the liquid-condition detection sensor of the present invention encompasses a liquid-condition detection sensor which does not necessarily include a control circuit.

This application is based on Japanese Patent Application Nos. JP 2006-013737 filed Jan. 25, 2006 and JP 2006-316489 filed Nov. 24, 2006, incorporated herein by reference in their entirety.

What is claimed is:

1. A liquid-condition detection sensor, at least a portion of which is to be immersed in a liquid to be measured, and which is adapted to detect a condition of the liquid to be measured, comprising:
   a sensor element, at least a portion of which is to be immersed in the liquid to be measured;
   a terminal member fixedly attached to the sensor element;
   an electrically conductive path member connected to the terminal member and electrically communicating with the sensor element via the terminal member;
   a holder tube extending in a longitudinal direction of the sensor, directly or indirectly holding the sensor element at a distal end portion thereof, and surrounding at least a portion of the electrically conductive path member and at least a portion of the terminal member; and
   a separator intervening between the terminal member and the holder tube and insulating the terminal member and the holder tube from one another.

2. The liquid-condition detection sensor according to claim 1, wherein a plurality of the terminal members are fixedly attached to the sensor element, and
   wherein the separator includes an inter-terminal insulating portion intervening between the terminal members, thereby insulating the terminal members from one another.

3. The liquid-condition detection sensor according to claim 1, wherein the separator is formed from an elastic material and includes a terminal-holding portion which elastically holds the terminal member within the holder tube.

4. The liquid-condition detection sensor according to claim 1, wherein the sensor element is partially surrounded by the holder tube, and
   the separator includes an element-holding portion which holds the sensor element within the holder tube.

5. The liquid-condition detection sensor according to claim 4, wherein the separator including the element-holding portion is formed from an elastic material, and
   the element-holding portion elastically holds the sensor element.

6. The liquid-condition detection sensor according to claim 1, wherein the sensor element is partially surrounded by the holder tube,
   the separator is formed from an elastic material having a plurality of projecting portions projecting from an outer circumferential surface thereof and provided along the longitudinal direction of the sensor, and
   the projecting portions of the separator coming into contact with an inner circumferential surface of the holder tube such that at least a portion of the separator is elastically deformed radially inward, whereby the separator elastically holds the sensor element and the terminal member within the holder tube.

7. The liquid-condition detection sensor according to claim 3, wherein the separator includes an inner-tube engagement portion projecting from the outer circumferential surface thereof and having an outside diameter greater than an inside diameter of the holder tube, and
   the inner-tube engagement portion of the separator engages a distal end of the holder tube.

8. The liquid-condition detection sensor according to claim 1, wherein the sensor element is partially surrounded by the holder tube, and
   the separator includes an element abutment portion which abuts the sensor element and positions the sensor element within the separator along a proximal-end-distal-end direction.

9. The liquid-condition detection sensor according to claim 1, wherein the separator is formed from an elastic material and has a through-hole wall portion through which a through hole extends for accommodating at least either of the electrically conductive path member and the terminal member, and
   the through-hole wall portion has a slit which extends along the through hole from one end to the other end of the through hole and penetrates from an outer circumferential surface of the through-hole wall portion to the through hole, and wherein by opening the slit through deformation of the separator, at least either of the electrically conductive path member and the terminal member can be placed in the through hole through the slit.

10. The liquid-condition detection sensor according to claim 1, wherein the sensor element comprises a first ceramic layer; a second ceramic layer superposed on the first ceramic layer; and a heat-generating resistor disposed between the first ceramic layer and the second ceramic layer and having a resistance which varies with temperature; and
   said heat-generating resistor outputting an output signal indicative of a condition of the liquid to be measured when a voltage is applied to the heat-generating resistor or a current is passed through the heat-generating resistor via the terminal member.

11. The liquid-condition detection sensor according to claim 1, further comprising an outer tube extending in a longitudinal direction and radially surrounding the outside of the holder tube,
   wherein the outer tube and the holder tube form a level sensor portion therebetween, forming a capacitor whose capacitance varies with a level of the liquid to be measured.

12. The liquid-condition detection sensor according to claim 1, wherein the liquid to be measured is a urea aqueous solution.

* * * * *